United States Patent [19]
Kitou et al.

[11] Patent Number: 5,993,436
[45] Date of Patent: Nov. 30, 1999

[54] INDWELLING CATHETER WITH IMPROVED KINKING RESISTANCE

[75] Inventors: Hideaki Kitou; Yoshihide Toyokawa; Takayasu Shimazaki; Kenji Ishikawa, all of Kanagawa-ken, Japan

[73] Assignee: Terumo Kabushiki Kaisha, Tokyo, Japan

[21] Appl. No.: 09/184,648

[22] Filed: Nov. 3, 1998

[30] Foreign Application Priority Data

Nov. 10, 1997 [JP] Japan ................................ 9-306262
Jul. 31, 1998 [JP] Japan ................................ 10-216914

[51] Int. Cl.⁶ .................................................. A61M 25/00
[52] U.S. Cl. .................................. 604/531; 604/265
[58] Field of Search .................................. 604/282, 531, 604/280, 264, 265

[56] References Cited

U.S. PATENT DOCUMENTS 5,226,899 7/1993 Lee et al. .
5,453,099 9/1995 Lee et al. .

*Primary Examiner*—Wynn Wood Coggins
*Assistant Examiner*—Eric Kline
*Attorney, Agent, or Firm*—Burns, Doane, Swecker & Mathis, LLP

[57] ABSTRACT

An indwelling catheter is made of a polyurethane resin having a Shore hardness of 60D or more. The soft segment of the polyurethane resin is constituted by polycaprolactone. The indwelling catheter has a kinking resistance of 10 mm or more when measured at 37° C. in wet state. The Young's modulus is at first 20 kgf/mm² or more when measure at 25° C. in dry state, and reduces to 15 kgf/mm² or less by soaking it in water of 37° C. for 5 minutes or less.

8 Claims, 3 Drawing Sheets

INDWELLING CATHETER WITH IMPROVED KINKING RESISTANCE

BACKGROUND OF THE INVENTION

The present invention relates to an indwelling catheter, more specifically relates to an indwelling catheter to be left in place in a blood vessel to perform infusion, introduction of a medicinal solution, blood transfusion, blood collection, monitor of blood circulation, etc.

An indwelling needle for use in infusion, transfusion, etc. has a catheter tubing made of a biocompatible, blood-compatible plastic, etc., and is left in a blood vessel with a distal end communicated with a tube extending from a receptacle, such as a infusion bag, containing a fluid, medicinal solution, blood, etc. Some type of the indwelling needle has a sharp-tipped internal needle made of a metal, etc. which longitudinally extends through inside the indwelling catheter and is integrated with the body portion of the indwelling catheter. This type of indwelling needle is inserted into a blood vessel together with the internal needle which is then withdrawn from the catheter to conduct the infusion, transfusion, etc. in the same manner as above.

Since the lumen of the catheter inserted in position in a body cavity must be maintained large enough to effectuate the infusion and introduction of medicinal solution which are the primary use of the indwelling needle, the catheter is required to have a high kinking resistance. Further, the catheter is required to be balanced in stiffness for the insertion into a blood vessel and pliability subsequent to the insertion, because the mechanical properties of the catheter largely affect the puncture of skin, the insertion of the catheter into a body cavity and the injury in wall of blood vessel during the insertion and the emplacement of the catheter.

The catheter used in the conventional indwelling needle has been mainly made of a fluorine resin such as polytetrafluoroethylene, ethylene-tetrafluoroethylene copolymer, etc. Although, the catheter made of a fluorine resin is sufficiently stiff for ease of the puncture of a skin and the insertion of the catheter into a blood vessel, it does not sufficiently soften in contact with blood. Therefore, there remains a fear of injuring the inner wall of the blood vessel. Also, since such a catheter is insufficient in the kinking resistance, there may be a fear of collapsing the passage for fluid flow.

Recently, a polyurethane resin having a soft segment of polyether has come to be used as the material for the catheter. U.S. Pat. No. 5,226,899 discloses a method of controlling the balance between the stiffness for inserting the catheter into a body cavity and the pliability after the insertion by using a catheter made of a hydrophilic polyetherurethane which softens upon contacting with a body fluid. However, the indwelling catheter made of polyetherurethane does not exhibit a sufficient kinking resistance even after the insertion into a body cavity such as a blood vessel, although it becomes pliable in contact with blood. When the catheter is made stiffer for ease of insertion, the kinking resistance is further deteriorated.

OBJECT AND SUMMARY OF THE INVENTION

The present invention addresses the above problem, and an object of the present invention is to provide an indwelling catheter having a stiffness for ease of insertion on one hand and a pliability after the insertion on the other hand as well as a good kinking resistance.

As a result of the intense research in view of the above object, the inventors have found that an indwelling catheter made of a polyurethane resin having a soft segment of polycaprolactone has a kinking resistance of 10 mm or more at 37° C. in wet state when measured in a manner as hereinbelow described. The polyurethane resin preferably has a Shore hardness of 60D or higher. The Young's modulus of the indwelling catheter is preferably 20 kgf/mm$^2$ or higher when measured at 25° C. in dry state for ease of insertion, and preferably reduces to 15 kgf/mm$^2$ or less after soaking in water of 37° C. within 5 minutes in view of preventing injury of the inner wall of blood vessel.

Thus, in a first aspect of the present invention, there is provided an indwelling catheter made of a polyurethane resin comprising a hard segment and a soft segment, the soft segment being polycaprolactone and the indwelling catheter having a kinking resistance of 10 mm or more when measured at 37° C. in wet state.

DETAILED DESCRIPTION OF THE INVENTION

The material for the indwelling catheter of the present invention is a polyurethane resin which is the product from a reaction of a diisocyanate, polycaprolactone and a chain extender.

Polycaprolactone may have a molecular weight of about 500 to 3000, preferably about 1000 to 2000, and commercially available from a variety of sources.

Diisocyanate may be an aromatic diisocyanate such as diphenylmethane-4,4'-diisocyanate and diphenylmethane-3,3'-diisocyanate; an alicyclic diisocyanate such as isophorone diisocyanate and dicyclohexylmethane-4,4'-diisocyanate; and an aliphatic diisocyanate such as hexamethylene diisocyanate. Of the above diisocyanates, diphenylmethane-4,4'-diisocyanate is most preferable.

Known chain extenders such as low molecular weight, diol, diamine or amino alcohol of up to 10 carbon atoms may be used alone or in combination. Examples for the chain extender may be 1,4-butanediol, ethylene glycol, diethylene glycol, triethylene glycol, 1,2-propanediol, 1,3-propanediol, 1,6-hexanediol, 1,4-bis-hydroxymethylcyclohexane, hydroquinone dihydroxyethyl ether, 1,6-hexane diamine and ethanolamine. Most preferred are 1,4-butanediol and 1,6-hexanediol.

The contents of respective components in the polyurethane resin are 20–45 weight %, preferably 27–41 weight % for the polycaprolactone; 42–62 weight %, preferably 45–56 weight % for the diisocyanate; and 13–18 weight %, preferably 14–17 weight % for the chain extender, each based on the total weight of the above components. Each content may be suitably selected from the above ranges so that the total may be 100 weight %.

The polyurethane resin comprises a hard segment and a soft segment, in which the soft segment is dominantly polycaprolactone. The weight ratio of the soft segment to the hard segment is 28/72 to 50/50, preferably 32/68 to 45/55. By using polycaprolactone and regulating the soft segment/hard segment weight ratio within the above range, the resultant indwelling catheter has a suitable balance between the stiffness and pliability as well as a good kinking resistance.

The polyurethane resin preferably has a Shore hardness of 60D or more for ease of puncturing a skin and inserting the indwelling catheter into a blood vessel. When less than 60D, the puncture and the insertion are not operated easily due to an insufficient stiffness. When larger than 85D, the moldability of the polyurethane resin by extrusion becomes poor thereby failing to obtain a indwelling catheter with a desired shape. Practically, the Shore hardness is preferably 65D to 80D.

The polyurethane resin may be prepared by a polymerization procedure known in the art such as prepolymer process and one-shot process preferably without adding a polymerization catalyst which may cause deleterious effects when the indwelling catheter comes into contact with a blood.

In the present invention, the kinking resistance is defined as follows.

Figure 3:
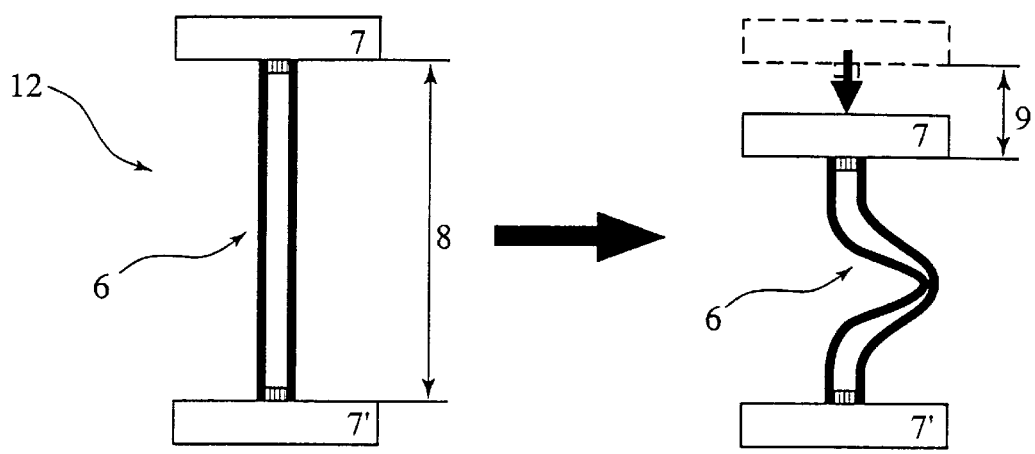
FIG. 3 is a schematic cross-sectional view illustrating the compression test to determine the kinking resistance of an indwelling catheter.

The kinking resistance of the indwelling catheter was measured by a compression tester 12 as shown in FIG. 3. The compression tester 12 comprises an upper clamp 7 movable upward and downward at a constant rate and a lower stationary clamp 7' disposed below the upper clamp 7. A catheter tube 6 with a predetermined length 8 was supported between the clamps 7, 7'. Then, the upper clamp 7 was allowed to move downward to apply axial compressing force to the catheter tube 6. The change in the load on the catheter tube 6 were automatically recorded on a chart as a function of the moving distance of the upper clamp 7. First, the measurement was made at 25° C. in dry state (about 30–70% relative humidity). Then the measurement was repeated at 37° C. in wet state (about 30–70% relative humidity) after soaking the catheter tube in water of 37° C. for a predetermined period of time. The size of the catheter tube measured was 25 mm in length, 0.65±0.02 mm in inner diameter and 0.88±0.02 mm in outer diameter in order to measure the kinking resistance. The moving rate of the upper clamp 7 was kept constant at 50 mm/min.

Figure 4:
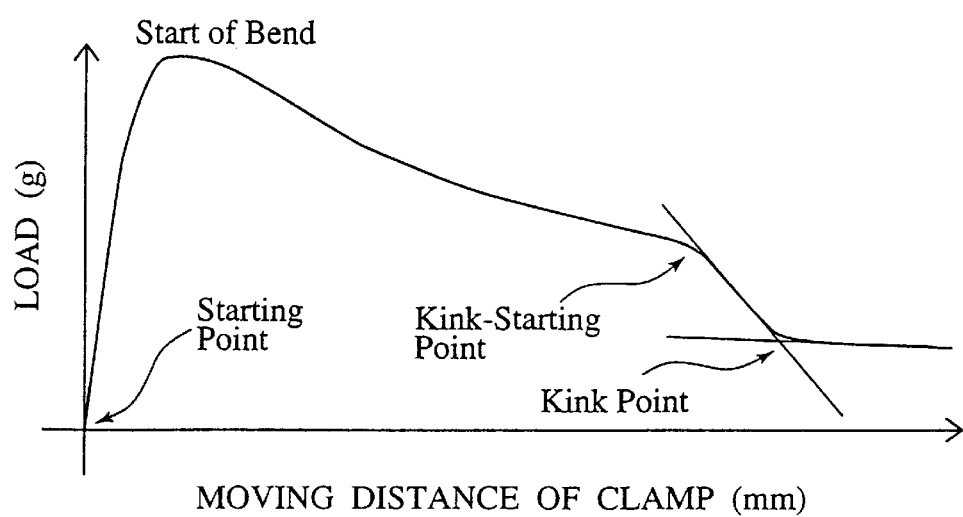
FIG. 4 is a curve showing the change in the load on an indwelling catheter during the measurement of the kinking resistance.

As the catheter tube 6 is compressed in the axial direction by the downward motion of the upper clamp 7 as shown in FIG. 3, the load on the catheter tube 6 changes with increasing moving distance 9. The change in the load is shown in FIG. 4. Upon compressing the catheter in the axial direction, the load on the catheter steeply rises, and then gradually decreases when the catheter starts to bend (start of bend). By continuing the compression of the catheter (downward motion of the clamp 7), the lumen of the catheter starts to be collapsed to cause kink, and the load begins to decrease at a larger rate to create an inflection point (kink start point) in the load-moving distance curve. The load becomes nearly constant when the lumen is almost completely collapsed to create another inflection point in the curve. The kink point is defined as the intersection of two tangents as shown in FIG. 4. The kinking resistance is represented by the distance of the upper clamp 7 moved from the start of the measurement (starting point) to the complete collapse of the lumen (kink point).

The kinking resistance of the indwelling catheter of the present invention is preferably 10 mm or more, more preferably 12 mm or more, and most preferably 14 mm or more when measured at 37° C. in wet state.

The Young's modulus of the indwelling catheter of the present invention is preferably 20 kgf/mm$^2$ or more, more preferably 25 kgf/mm$^2$ or more, when measured at 25° C. in dry state, for ease of the puncture and insertion. To prevent the injury of the blood vessel wall after the insertion of the catheter, the Young's modulus is preferred to be reduced to 15 kgf/mm$^2$ or less, preferably 10 kgf/mm$^2$ or less by the soaking in water of 37° C. for 5 minutes or less. The Young's modulus was measured by a tensile tester, Strograph T manufactured by Toyo Seiki Seisakusho Co. Ltd. Like the measurement of the kinking resistance, the tensile test was conducted at 25° C. in dry state (about 30–70% relative humidity) and at 37° C. in wet state (about 30–70% relative humidity) after soaking the indwelling catheter in water of 37° C. for a predetermined period of time under the conditions of a gage distance of 10 mm and a stress rate of 5 mm/min. The Young's modulus was calculated from the straight line portion of the tensile stress-strain curve thus obtained.

Figure 1:
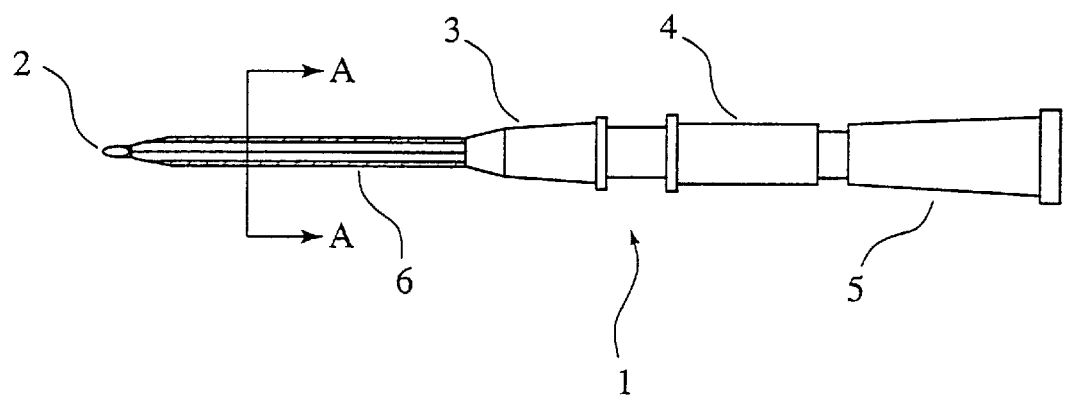
FIG. 1 is a schematic view, partly broken away, showing an indwelling needle fitted with the indwelling catheter of the present invention.

FIG. 1 shows a nonlimitative example of the indwelling needle fitted with the indwelling catheter of the present invention. The catheter 6 is attached to a hub 3 by a caulking pin (not shown). An internal needle 2 attached to one end of a needle hub 4 is coaxially inserted into the lumen of the indwelling catheter 6. A filter cap 5 is disposed to the other end of the needle hub 4.

The thickness of the wall of the indwelling catheter is preferably 0.105–0.125 mm, and the length is preferably 25–32 mm while depending on the use thereof.

Figure 2:
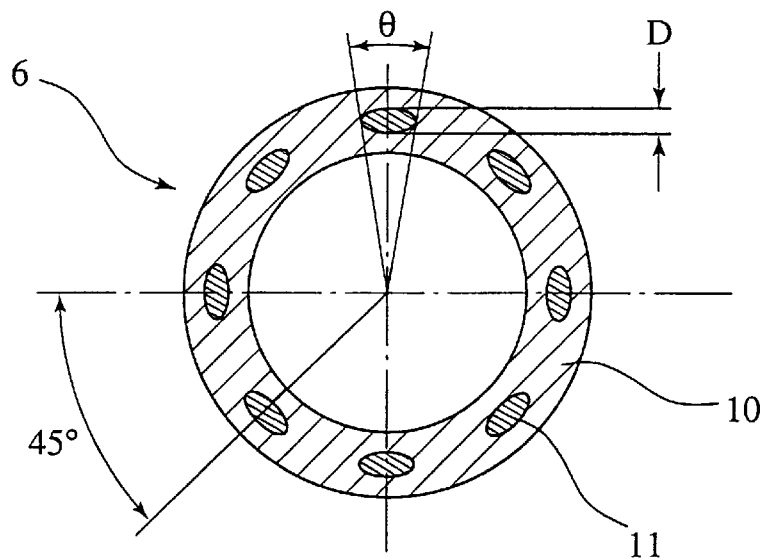
FIG. 2 is a cross-sectional view showing the indwelling catheter of FIG. 1 taken along the line A—A.

As shown in FIG. 2, the indwelling catheter of the present invention may have at least one stripe 11 of a polyurethane containing an X-ray-opaque agent as a visualizing aid to easily find the position of the indwelling catheter when fragments of the indwelling catheter formed by rupture are left in a blood vessel. The stripe extends longitudinally along at least a portion of the catheter length and is encapsulated in a catheter wall 10. The stripe may be easily formed by a known coextrusion of the polyurethane resin for the catheter wall and a polyurethane for the stripes added with the X-ray-opaque agent such as barium sulfate, tungsten, bismuth oxide, bismuth subcarbonate, gold, etc. preferably in an amount of 10–80 weight % based on the polyurethane. The polyurethane for the stripes may be any polyurethane conventionally used as the material of the catheter. Also, the polyurethane for the stripes may be the same as the polyurethane for forming the catheter wall. The cross-sectional shape of the stripe is not limited and it may be formed into any convenient shape such as circle shape, elliptical shape, etc. by suitably selecting the design of the coextrusion die. The number of the stripes is also not limited, and usually 1–12. The thickness D of the stripe is preferably 60–80% the thickness of the indwelling catheter wall 10. The width W of the stripe is preferably regulated so that a visual angle θ with respect to the axis of the catheter may be 10–30 degree.

As described above, since the indwelling catheter of the present invention is made of a polyurethane resin in which the soft segment is dominantly polycaprolactone, a kink resistance thereof is 10 mm or more at 37° C. in wet state thereby to ensure the passage for a fluid flow after being left in position in a body cavity such as a blood vessel. Unlike the know catheters, the indwelling catheter of the invention exhibits a sufficient stiffness during the puncture and insertion operation and softens without deteriorating the kink resistance immediately after being left in a blood vessel, thereby to effectively prevent the blood vessel from being injured.

The present invention will be further described while referring to the following Examples which should be considered to illustrate various preferred embodiments of the present invention.

EXAMPLE 1

As the material for the catheter tube, a polyurethane resin (polycaprolactone:diphenylmethane-4,4'-diisocyanate:1,4-butanediol=37:48:15 by weight) having a Shore hardness of 68D was used. As the material for stripes, a polyurethane resin (polycaprolactone:diphenylmethane-4,4'-diisocyanate:1,4-butanediol=32:52:16 by weight) having a Shore hardness of 74D added with 30 weight % barium sulfate was used. The above resin materials were coextruded to obtain a striped indwelling catheter as shown in FIG. 2, which had eight stripes, an inner diameter of 0.65 mm, an outer diameter of 0.88 mm and a useful length of 25 mm.

Figure 5:
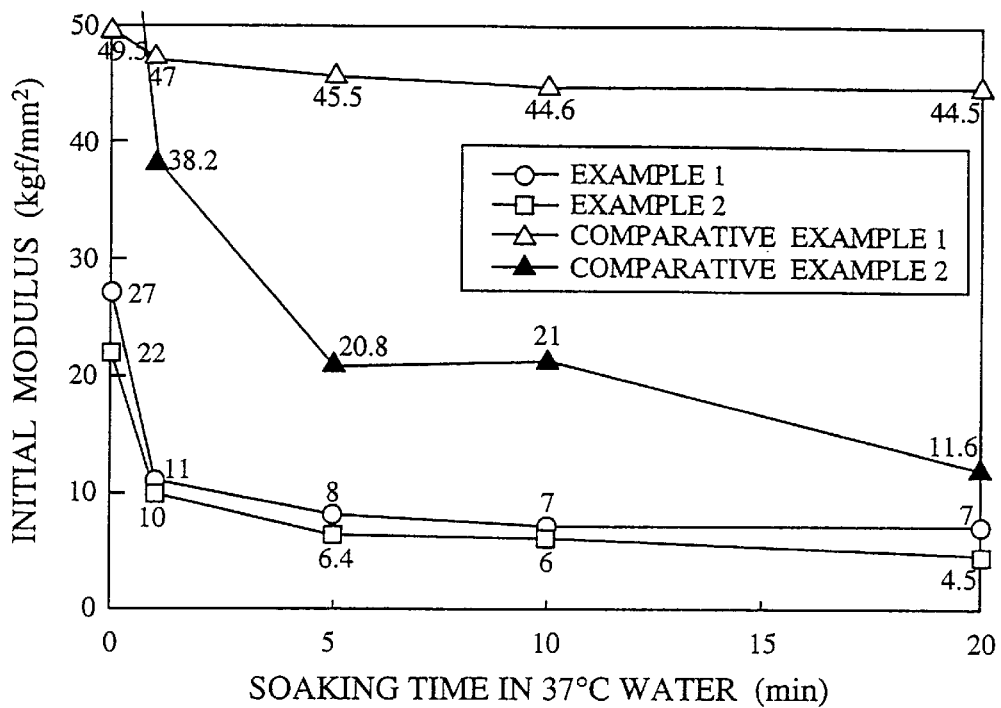
FIG. 5 is a graph showing the results of the Young's modulus measurements on the indwelling catheters of the invention and the conventional catheters.

The indwelling catheter thus obtained was subjected to the tensile test in the manner as described above to determine the Young's modulus. The results are shown in FIG. 5. The Young's modulus was 27 kgf/mm$^2$ when measured at 25° C. in dry state (corresponding to a soaking time of zero minute in FIG. 5) and immediately reduced to 8 kgf/mm$^2$ after 5-minute soaking in water of 37° C. to show that the indwelling catheter exhibited at first a sufficient stiffness for ease of the puncture and insertion, and then exhibited a suitable pliability in contact with the water.

Figure 6:
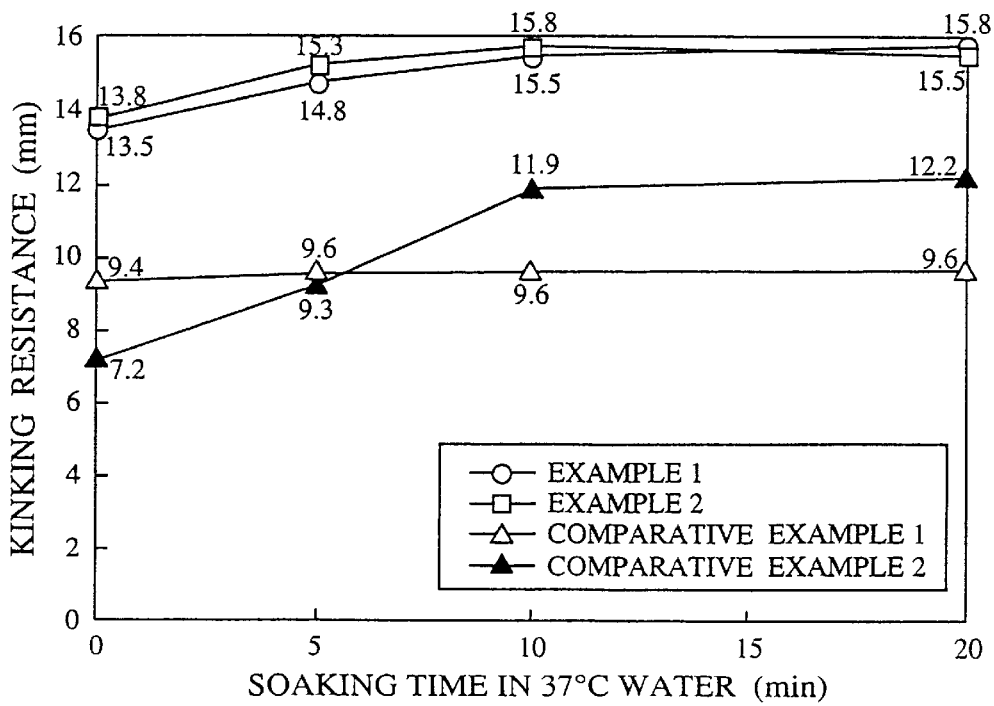
FIG. 6 is a graph showing the results of the kinking resistance measurements on the indwelling catheters of the invention and the conventional catheters.

The kinking resistance was measured using a material testing machine, Autograph AGS-100A manufactured by Shimadzu Corporation in the manner as described above. The results are shown in FIG. 6. The kinking resistance was larger than 10 mm in any case of measurements at 25° C. in dry state (corresponding to a soaking time of zero minute in FIG. 5) and 37° C. in wet state after 5-minute, 10-minute and 20-minute soaking in water of 37° C.

EXAMPLE 2

A striped indwelling catheter of 0.65 mm in inner diameter, 0.88 mm in outer diameter and 25 mm in useful length was obtained in the same manner as in Example 1 while using, as the material for the catheter wall, a polyurethane resin (polycaprolactone:diphenylmethane-4,4'-diisocyanate:1,4-butanediol=37:48:15 by weight) having a Shore hardness of 68D, and as the material for stripes, a polyurethane resin (polycaprolactone:diphenylmethane-4,4'-diisocyanate:1,4-butanediol=37:48:15 by weight) having a Shore hardness of 68D added with 30 weight % barium sulfate.

The Young's modulus and the kinking resistance of the indwelling catheter thus obtained were measured in the same manner as in Example 1. The results are shown in FIGS. 5 and 6, respectively. The Young's modulus was 22 kgf/mm$^2$ when measured at 25° C. in dry state and immediately reduced to 6.4 kgf/mm$^2$ after 5-minute soaking in water of 37° C. to show that the indwelling catheter exhibited at first a sufficient stiffness for ease of the puncture and insertion and then exhibited a suitable pliability in contact with the water. The kinking resistance was larger than 10 mm in any case of measurements at 25° C. in dry state and 37° C. in wet state after 5-minute, 10-minute and 20-minute soaking in water of 37° C.

EXAMPLE 3

A striped indwelling catheter of 0.65 mm in inner diameter, 0.88 mm in outer diameter and 25 mm in useful length was obtained in the same manner as in Example 1 while using, as the material for the catheter wall, a polyurethane resin (polycaprolactone:diphenylmethane-4,4'-diisocyanate:1,4-butanediol=41:45:14 by weight) having a Shore hardness of 64D, and as the material for stripes, a polyurethane resin (polycaprolactone:diphenylmethane-4,4'-diisocyanate:1,4-butanediol=37:48:15 by weight) having a Shore hardness of 68D added with 30 weight % barium sulfate.

The kinking resistance of the indwelling catheter, measured in the same manner as in Example 1, was 14.5 mm at 25° C. in dry state and 14.9 mm at 37° C. in wet state after 10-minute soaking in water of 37° C.

EXAMPLE 4

A non-striped indwelling catheter of 0.66 mm in inner diameter, 0.89 mm in outer diameter and 25 mm in useful length was obtained in the same manner as in Example 1 while using a polyurethane resin (polycaprolactone:diphenylmethane-4,4'diisocyanate:1,4-butanediol=32:52:16 by weight) having a Shore hardness of 74D.

The Young's modulus and the kinking resistance of the catheter thus obtained were measured in the same manner as in Example 1. The puncture and insertion operation was easy because the Young's modulus was 28 kgf/mm$^2$ at 25° C. in dry state. The Young's modulus reduced to 12 kgf/mm$^2$ at 37° C. in wet state after 5minute soaking in water of 37° C. to show a sufficient pliability. The kinking resistance was 13.5 mm at 25° C. in dry state, and 13.9 mm at 37° C. in wet state after 10-minute soaking in water of 37° C.

COMPARATIVE EXAMPLE 1

The Young's modulus and the kinking resistance of a non-striped catheter (0.64 mm in inner diameter, 0.83 mm in outer diameter, and 25 mm in useful length made of ethylene-tetrafluoroethylene resin) used in an indwelling needle SURFLO OT® (Terumo Corporation) were measured in the same manner as in Example 1. The results are shown in FIGS. 5 and 6, respectively.

Although the puncture and insertion operation was easy due to a sufficient stiffness, the catheter did not soften even after 20-minute soaking in water of 37° C. Also, the catheter was poor in the kinking resistance, because it was less than 10 mm in any case of the measurements at 25° C. in dry state and 37° C. in wet state after 5-minute, 10-minute and 20-minute soaking in water of 37° C.

COMPARATIVE EXAMPLE 2

The same measurements of the Young's modulus and the kinking resistance as in Example 1 were made on a commercially available catheter (Insyte available from Becton Dickinson and Company, 0.65 mm in inner diameter, 0.88 mm in outer diameter and 25 mm in useful length) made of a polyetherurethane and having 6 stripes made of the same polyetherurethane added with 50 weight % barium sulfate. The results are shown in FIGS. 5 and 6. The catheter did not sufficiently soften even after 10-minute soaking to exhibit an Young's modulus as high as about 21 kgf/mm², and easily caused the kink.

COMPARATIVE EXAMPLE 3

A non-striped indwelling catheter of 0.66 mm in inner diameter, 0.89 mm in outer diameter and 25 mm in useful length was obtained in the same manner as in Example 1 while using a polyurethane resin (polycarbonate:diphenylmethane-4,4'-diisocyanate:1,4-butanediol=36:53:11 by weight) having a Shore hardness of 53D. The results of the measurements showed that the catheter thus obtained had a Young's modulus of 9.3 kgf/mm² at 25° C. in dry state, and 1.9 kgf/mm² at 37° C. in wet state after 10-minute soaking in water of 37° C. Since the catheter was highly pliable in dry state, the puncture and insertion operation was practically impossible.

What is claimed is:

1. An indwelling catheter made of a polyurethane resin comprising a hard segment and a soft segment, said soft segment being polycaprolactone and said indwelling catheter having a kinking resistance of 10 mm or more when measured at 37° C. in wet state.

2. The indwelling catheter according to claim 1, wherein said polyurethane resin has a Shore hardness of 60D or higher.

3. The indwelling catheter according to claim 2, wherein said polyurethane resin has a Shore hardness of 65D–80D.

4. The indwelling catheter according to claim 1, wherein said indwelling catheter has at least one stripe encapsulated in a wall of said indwelling catheter, said stripe being made of a polyurethane resin added with an X-ray-opaque agent.

5. The indwelling catheter according to claim 4, wherein said at least one stripe has a thickness 60–80% of a thickness of a wall of said indwelling catheter.

6. The indwelling catheter according to claim 1, wherein a Young's modulus is 30 kgf/mm² or more when measured at 25° C. in dry state and reduces to 15 kgf/mm² or less at 37° C. in wet state by soaking said indwelling catheter in water of 37° C. for 5 minutes or less.

7. The indwelling catheter according to claim 1, wherein a weight ratio of said soft segment to said hard segment is 28/72 to 50/50.

8. The indwelling catheter according to claim 1, wherein the polycaprolactone has a molecular weight of about 500–3000.

* * * * *

UNITED STATES PATENT AND TRADEMARK OFFICE
CERTIFICATE OF CORRECTION

PATENT NO. : 5,993,436
DATED : November 30, 1999
INVENTOR(S) : Hideaki KITOU et al It is certified that error appears in the above-indentified patent and that said Letters Patent is hereby corrected as shown below:

In Column 3, line 41, delete "change" and insert -- changes --.
In Column 5, line 3, delete "know" and insert -- known --.
In Column 7, line 23, after "state" and before ".", insert -- , wherein said polyurethane resin is a reaction product of a monomer mixture comprising 20-45 weight % of polycaprolactone, 42-62 weight % of a diisocyanate and 13-18 weight % of a low-molecular weight diol --.

Signed and Sealed this

Third Day of October, 2000

Attest:

Q. TODD DICKINSON

*Attesting Officer*          *Director of Patents and Trademarks*